(12) United States Patent
Lin (10) Patent No.: US 6,926,698 B2
(45) Date of Patent: Aug. 9, 2005

(54) SAFE COVER DEVICE FOR THE NEEDLE OF A SYRINGE

(76) Inventor: Bih-Chern Lin, 5F-6, No. 8, Lane 133, Chung Te Rd., Sec. 1, Taichung (TW)

( * ) Notice: Subject to any disclaimer, the term of this patent is extended or adjusted under 35 U.S.C. 154(b) by 450 days.

(21) Appl. No.: 10/101,067

(22) Filed: Mar. 20, 2002

(65) Prior Publication Data

US 2003/0181862 A1 Sep. 25, 2003

(51) Int. Cl.[7] ................................................ A61M 5/32
(52) U.S. Cl. ...................... 604/198; 604/110; 604/263; 128/919
(58) Field of Search ................................ 604/110, 187, 604/192, 197, 198, 263; 128/919

(56) References Cited

U.S. PATENT DOCUMENTS

| | | | | |
|---|---|---|---|---|
| 4,695,274 A | * | 9/1987 | Fox | 604/198 |
| 5,300,038 A | * | 4/1994 | Haber et al. | 604/187 |
| 5,318,547 A | * | 6/1994 | Altschuler | 604/198 |
| 5,514,107 A | * | 5/1996 | Haber et al. | 604/197 |
| 5,591,138 A | * | 1/1997 | Vaillancourt | 604/263 |
| 5,630,803 A | * | 5/1997 | Tamaro | 604/263 |
| 6,033,387 A | * | 3/2000 | Brunel | 604/198 |
| 6,183,445 B1 | * | 2/2001 | Lund et al. | 604/198 |
| 6,344,032 B1 | * | 2/2002 | Perez et al. | 604/198 |
| 6,416,497 B1 | * | 7/2002 | Kirk | 604/198 |
| 6,419,658 B1 | * | 7/2002 | Restelli et al. | 604/110 |
| 6,648,858 B2 | * | 11/2003 | Asbaghi | 604/198 |
| 2002/0156426 A1 | * | 10/2002 | Gagnieux et al. | 604/197 |

* cited by examiner

*Primary Examiner*—LoAn H. Thanh
(74) *Attorney, Agent, or Firm*—Troxell Law Office, PLLC (57) ABSTRACT

A safe cover device for the needle of a syringe comprising an external sleeve, a syringe clamp, a needle cap and an annular collar, of which the syringe clamp and the annular collar are combined with each other on a syringe, and the external sleeve is slipped over the syringe to completely accommodate the needle. So that when the needle cap covers the needle, stabbing of the needle and infection of germs can be avoided; thereby, the medical staff using the syringe can be protected. The device can be easily mounted and can be repeatedly used to reduce cost and get an environmental conservative effect.

7 Claims, 12 Drawing Sheets fig.1 fig. 2 fig. 3 fig. 4 fig. 5 fig. 6a fig. 6b fig. 7a fig. 7b fig. 8a fig. 8b fig. 9

SAFE COVER DEVICE FOR THE NEEDLE OF A SYRINGE

BACKGROUND OF THE INVENTION

1. Field of the Invention

The present invention is related to a safe cover device for the needle of a syringe, and especially to a device with an external sleeve to completely accommodate the needle, and with an annular collar to fit in a needle cap in order that the needle cap can be safely cover the needle, the device is particularly suitable to apply to a syringe or the like.

2. Description of the Prior Art

Since the medical science was widely developed, medicine injection with syringes has been the fastest and most effective way of curing, and it is widely adopted in the medical field. However, popularization of injection with syringes derivates problems of infection of germs by inadvertent stabbing, which problem has been gradually taken seriously, and various syringes have been developed thereby.

However, most conventional protecting structures for the needles of syringes have a sleeve for each needle generally in the shape of an elongate cylinder having a receiving chamber with a predetermined longitudinal depth for insertion therein of the needle of the corresponding syringe; the protecting sleeve is provided on the external surface thereof with a protective pick-up portion extending a predetermined length outwardly to allow a user to pick up with fingers, the protective pick-up portion has a predetermined distance from the external surface of the syringe to provide a safe distance when in picking up; however, with this safe distance from the syringe during picking up the protective pick-up portion by the user, the sleeve is hard to be actually aligned with the needle for inserting after use, it is more probable that cases of accident stabbing by the needle may occur; therefore, such conventional protecting structures are not desired.

In view of this, the inventor of the present invention studied and developed a safe cover device for the needle of a syringe which is safe in putting on a needle cap against stabbing, and is convenient for mounting and is able to be used repeatedly.

SUMMARY OF THE INVENTION

The primary object of the present invention is to provide a safe cover device for the needle of a syringe, wherein, by providing an external sleeve, dangerous pointed needle can be held therein to effectively prevent the needle from accident stabbing a medical staff in putting on the needle cap, and the needle cap can safely cover the needle.

The secondary object of the present invention is to provide a safe cover device for the needle of a syringe; the device can be mounted without changing the original structure of the syringe. Thereby an effect of safely putting on the needle cap can be achieved; and the device can suit needles of various lengths.

Another object of the present invention is to provide a safe cover device for the needle of a syringe, wherein, by the nature that an external sleeve and a syringe clamp can be easily mounted and dismantled as well as can be repeatedly used, the device has an economic and an environmental conservative effect.

To get the above object, the present invention comprises an external sleeve, a syringe clamp, a needle cap and an annular collar, of which the syringe clamp and the annular collar are combined with each other on a conventional syringe, and the external sleeve is slipped over the syringe to accommodate the needle completely or let the needle extend outwardly of the syringe. So that when the needle cap covers the needle, stabbing by the needle and infection of germs can be avoided, thereby, the medical staff using the syringe can be protected. The device can be easily mounted, the external sleeve and the syringe clamp of the device can be repeatedly used to reduce cost and get an environmental conservative effect.

The present invention will be apparent in its features and structure after reading the detailed description of the preferred embodiment thereof in reference to the accompanying drawings.

DETAILED DESCRIPTION OF THE PREFERRED EMBODIMENT

Referring to FIGS. 1–4, the safe cover device for the needle of a syringe of the present invention has an external sleeve 20, a syringe clamp 30, a needle cap 40 and an annular collar 50 mounted on a syringe 10.

Figure 1:
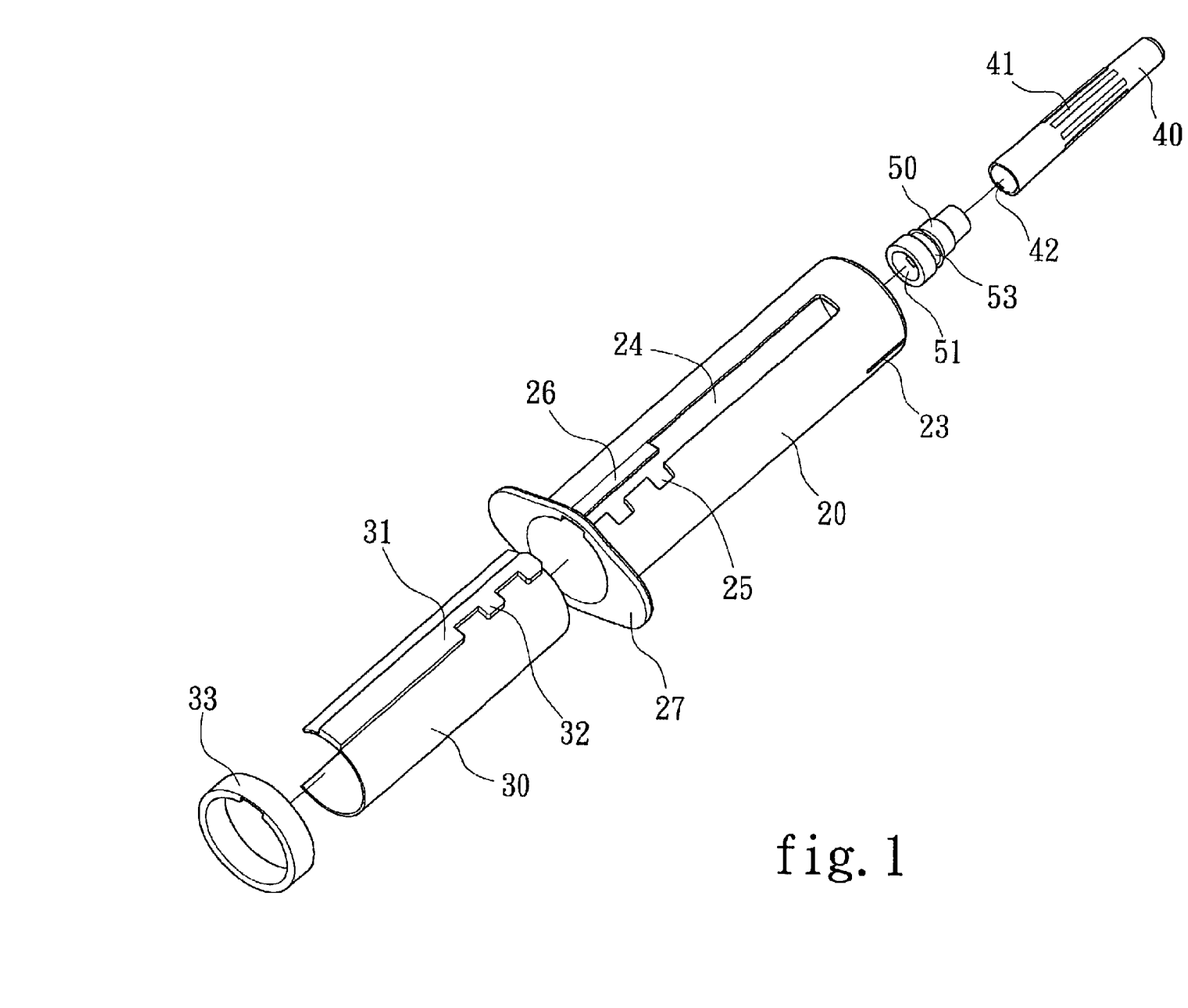
FIG. 1 is an analytic perspective view of an embodiment of the present invention.

Wherein, the syringe 10 is a conventional one, the front end thereof is provided with a needle 12 with a point 11.

The external sleeve 20 is a cylinder, and has internally a receiving camber in correspondence in shape with that of the syringe 10, it is provided on the top thereof with a conical surface 21 on which a central hole 22 and an axial cut 23 are provided to allow extending of the needle 12 therein. The external sleeve 20 is cut on the lateral side thereof to form an elongate slide slot 24 on which there are a plurality of engaging notches 25, the opposite side to the side with the engaging notches 25 is provided with a bendable positioning piece 26, the external sleeve 20 is provided on the bottom thereof with a plurality of flanges 27 for holding.

The syringe clamp 30 is a curved sheet with a curvature exactly for clamping the syringe 10. A protruding slide rail 31 is provided on and at an appropriate position of the surface of the syringe clamp 30, and is provided at appropriate positions thereon a plurality of recessed portions to form a plurality of engaging blocks 32. The syringe clamp 30 is provided on the tailing end thereof with a fixing ring 33 with a groove on the inner surface thereon for slipping over the syringe 10 and the syringe clamp 30, so that the syringe clamp 30 can firmly clamp the syringe 10.

The needle cap 40 is an elongate cylinder with a plurality of skid-proof knurls 41 on the surface thereof, and is provided on the inner edge of the opening thereof with a plurality of engaging nodes 42 to make engagement of the needle cap 40 with the annular collar 50.

The annular collar 50 is a hollow cylinder with a central bore 51 able to exactly fit over the needle 12 tightly, and is provided on the external surface thereof with an embedding groove 52 and an engaging groove 53; the embedding groove 52 makes engaging of the needle cap 40 with the annular collar 50, while the engaging groove 53 is provided for engaging the conical surface 21.

Figure 2:
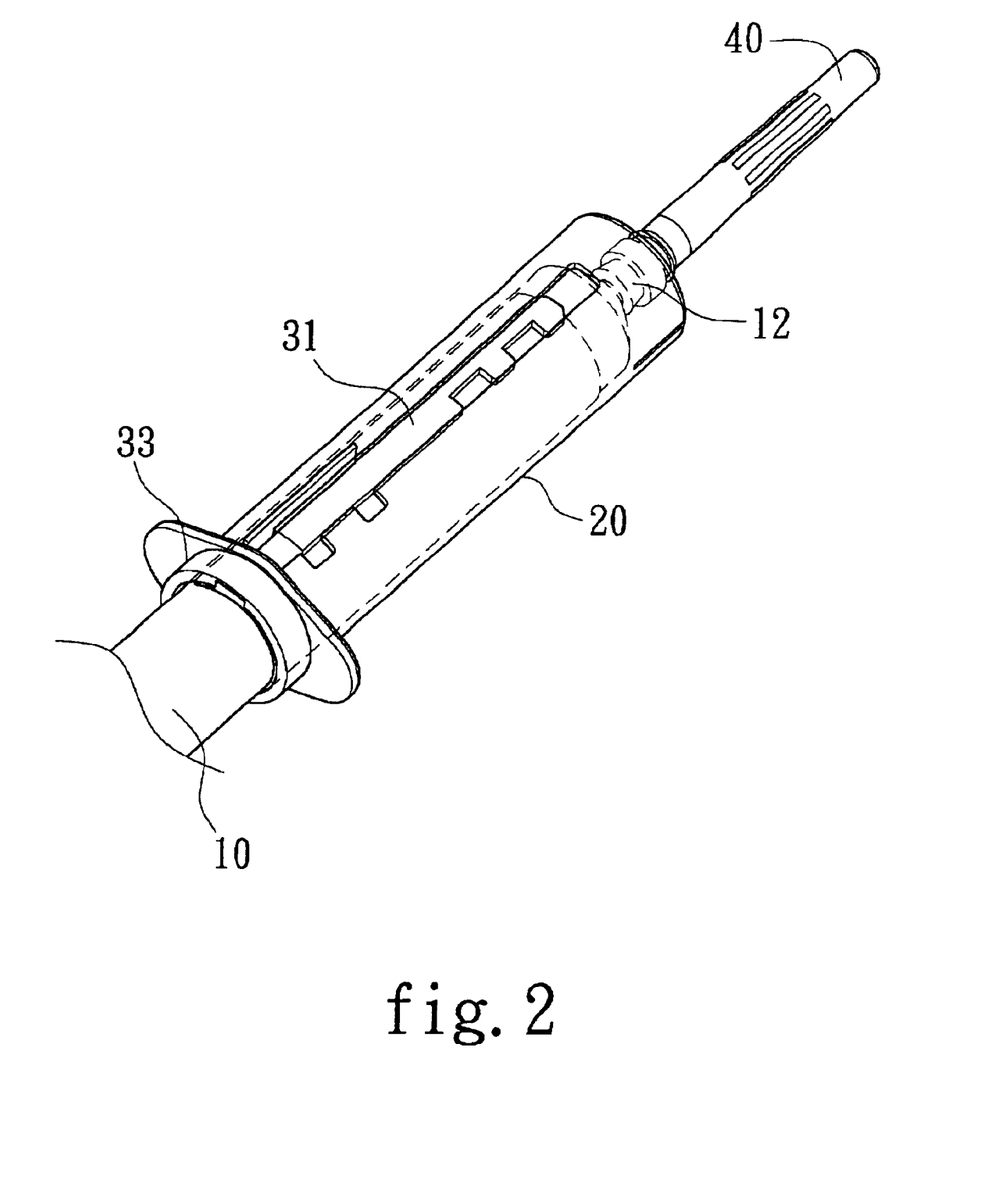
FIG. 2 is a perspective view of the embodiment of the present invention.

Referring to FIGS. 1, 2, when in assembling the present invention, the syringe clamp 30 is taken to clamp the syringe 10, the fixing ring 33 is taken to fit over the syringe 10. The syringe clamp 30 can firmly clamp the syringe 10, then the needle cap 40 integrally engages with the annular collar 50 by engagement of the engaging nodes 42 with the embedding groove 52. And then the needle cap 40 is slipped over the needle 12, the central bore 51 of the annular collar 50 is designed to fit tightly over the needle 12, hence the annular collar 50 can firmly hold the needle 12 by a suitable friction force. Lastly, referring to FIG. 3, the elongate slide slot 24 of the external sleeve 20 is aligned with the protruding slide rail 31 of the syringe clamp 30 to make fitting of the protruding slide rail 31 in the elongate slide slot 24. The needle 12 extends out of the external sleeve 20 through the central hole 22 of the latter; and the conical surface 21 engages in the engaging groove 53 of the annular collar 50. With the above stated structural assembling, the safe cover device for the needle of a syringe of the present invention is completed.

Figure 3:
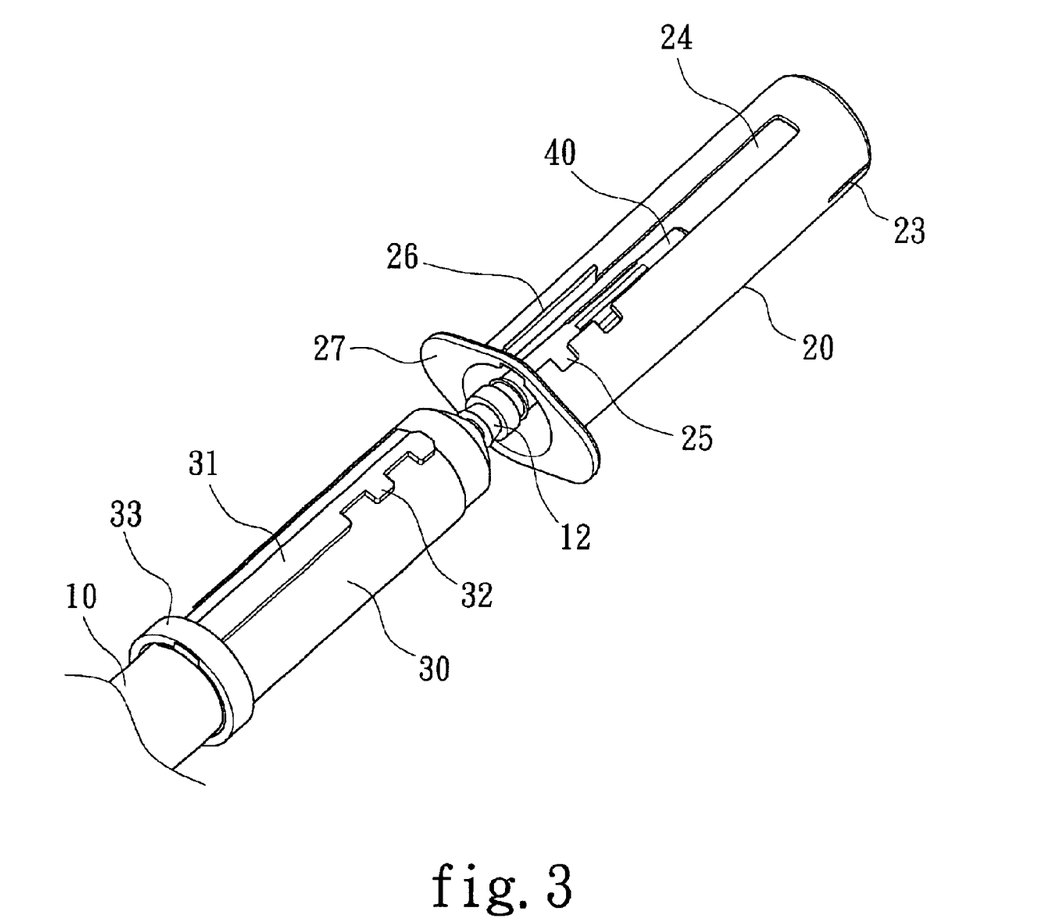
FIG. 3 is a schematic view showing the embodiment of the present invention is slipped over a syringe.
Figure 4:
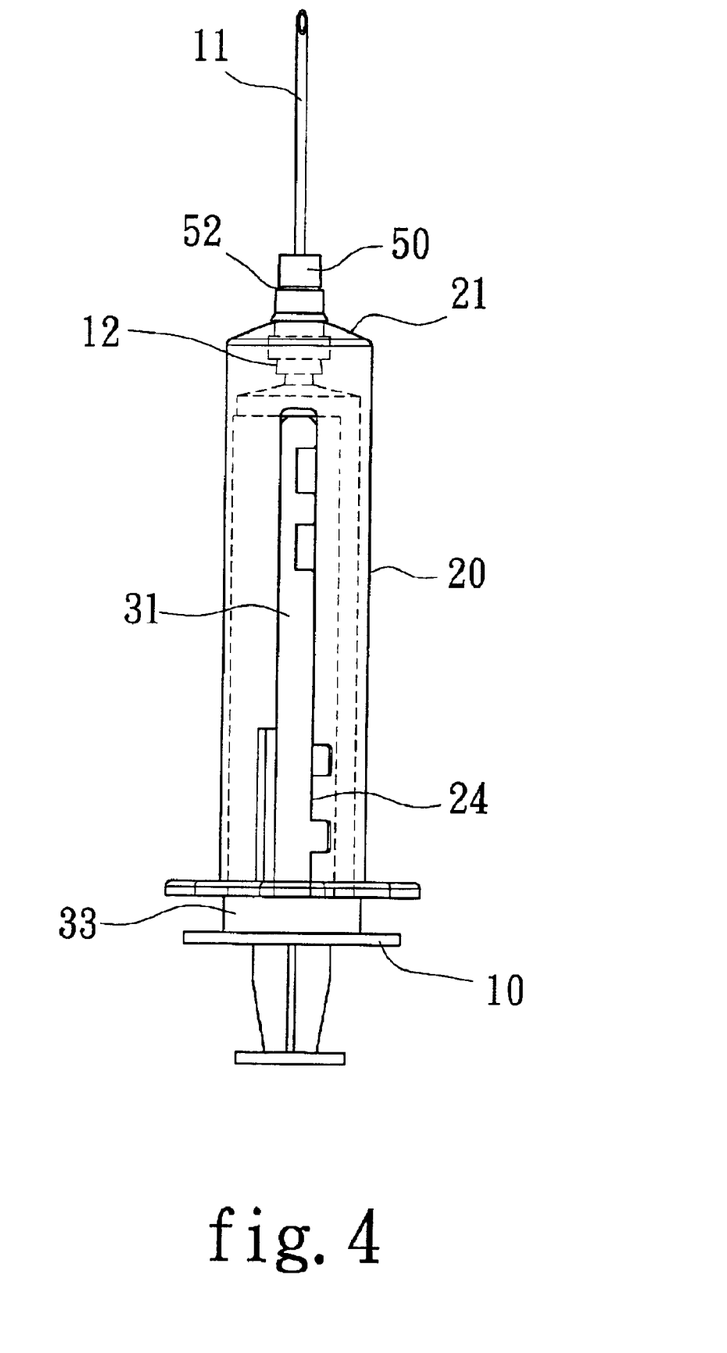
FIG. 4 is a schematic view showing the embodiment of the present invention is in injection of medicine.

Referring to FIGS. 3, 4, when in using the present invention, the syringe 10 having the syringe clamp 30, the annular collar 50 and the needle cap 40 is added therein appropriate medicine, and is slipped in the external sleeve 20 according to the mode stated above, the conical surface 21 is engaged in the engaging groove 53 of the annular collar 50. In this way, the syringe 10 is fixed in the external sleeve 20, while the needle 12 is exposed to the outside of the external sleeve 20, now the syringe 10 is ready for injection in a patient.

Figure 5:
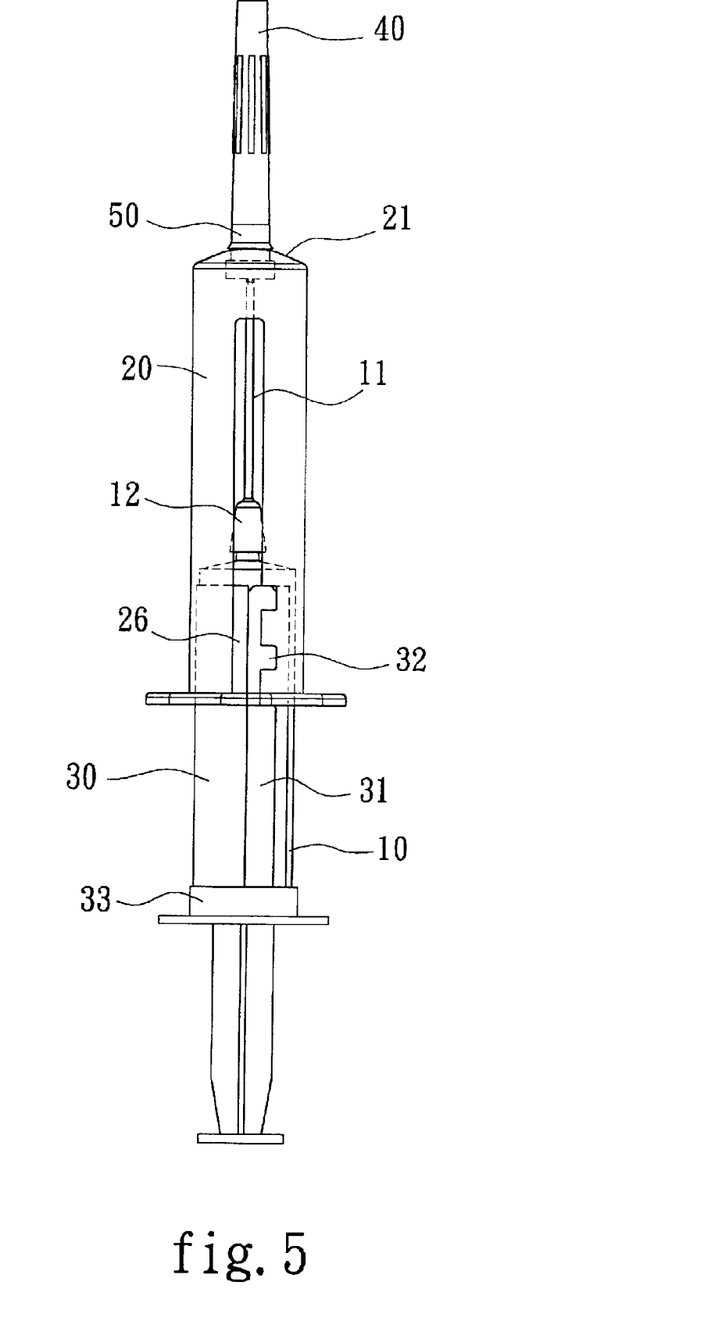
FIG. 5 is a schematic view showing the embodiment of the present invention when the needle thereof is held in an external sleeve.

Referring to FIG. 5, when the needle cap 40 is to be fitted over the needle 12 again after using of the syringe 10, the syringe 10 is pulled out in the first place to make separation of the annular collar 50 from the needle 12, and the point 11 of the needle 12 is contracted into the external sleeve 20 until the engaging blocks 32 on protruding slide rail 31 are aligned with the engaging notches 25 of the external sleeve 20; then the syringe 10 is rotated to make engagement of the engaging notches 25 with the engaging blocks 32, and the bendable positioning piece 26 is bent to stuff in the slide rail 31, thereby, the syringe 10 can be firmly engaged in the external sleeve 20 against dropping. Now, the needle 12 with the needlepoint 11 is completely accommodated in the external sleeve 20, thereby, when the needle cap 40 covers the needle 12, there will be completely no danger of stabbing by the needlepoint 11. The needle cap 40 is combined with the annular collar 50 safely, and the slide rail 31 sliding on the external sleeve 20 is provided with a plurality of engaging notches 25, the engaging notches 25 can be chosen appropriately to meet the length of the point 11 in order to be engaged therein the engaging blocks 32. In this way, the syringe 10 can have any needle 12 of any of various lengths.

Figure 6A:
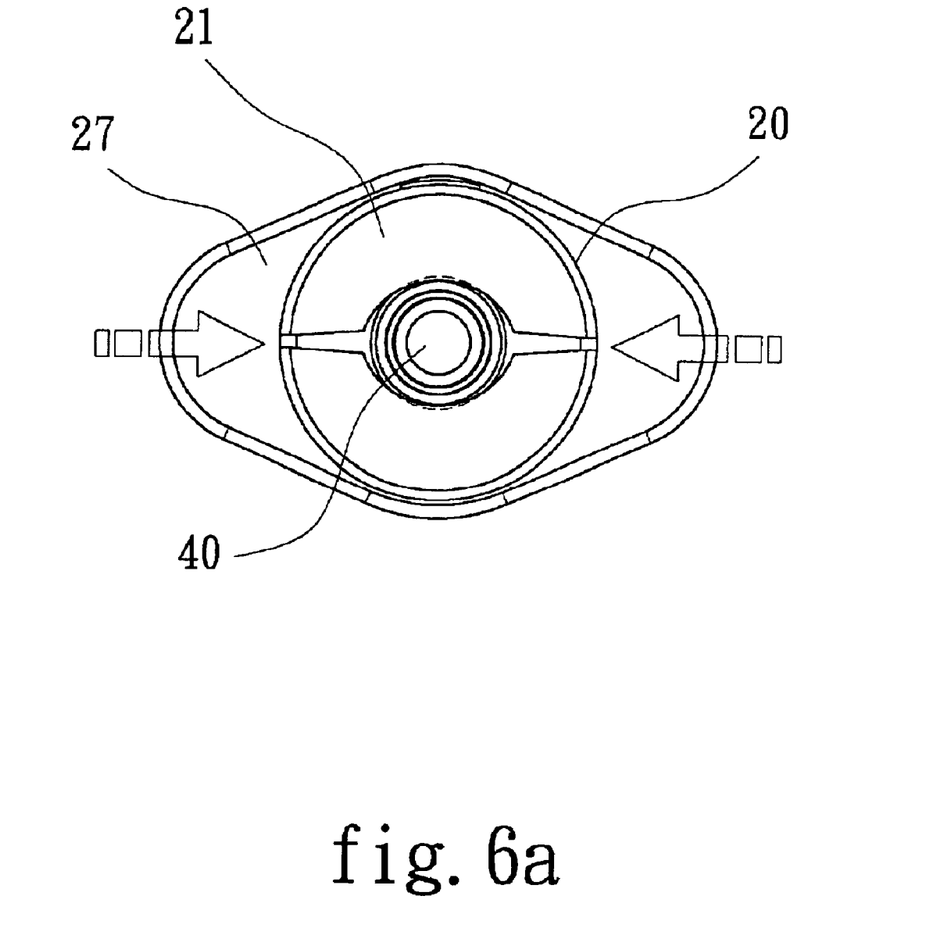
FIG. 6a is a schematic view showing that tapered surfaces of the embodiment of the present invention are under action of forces.
Figure 6B:
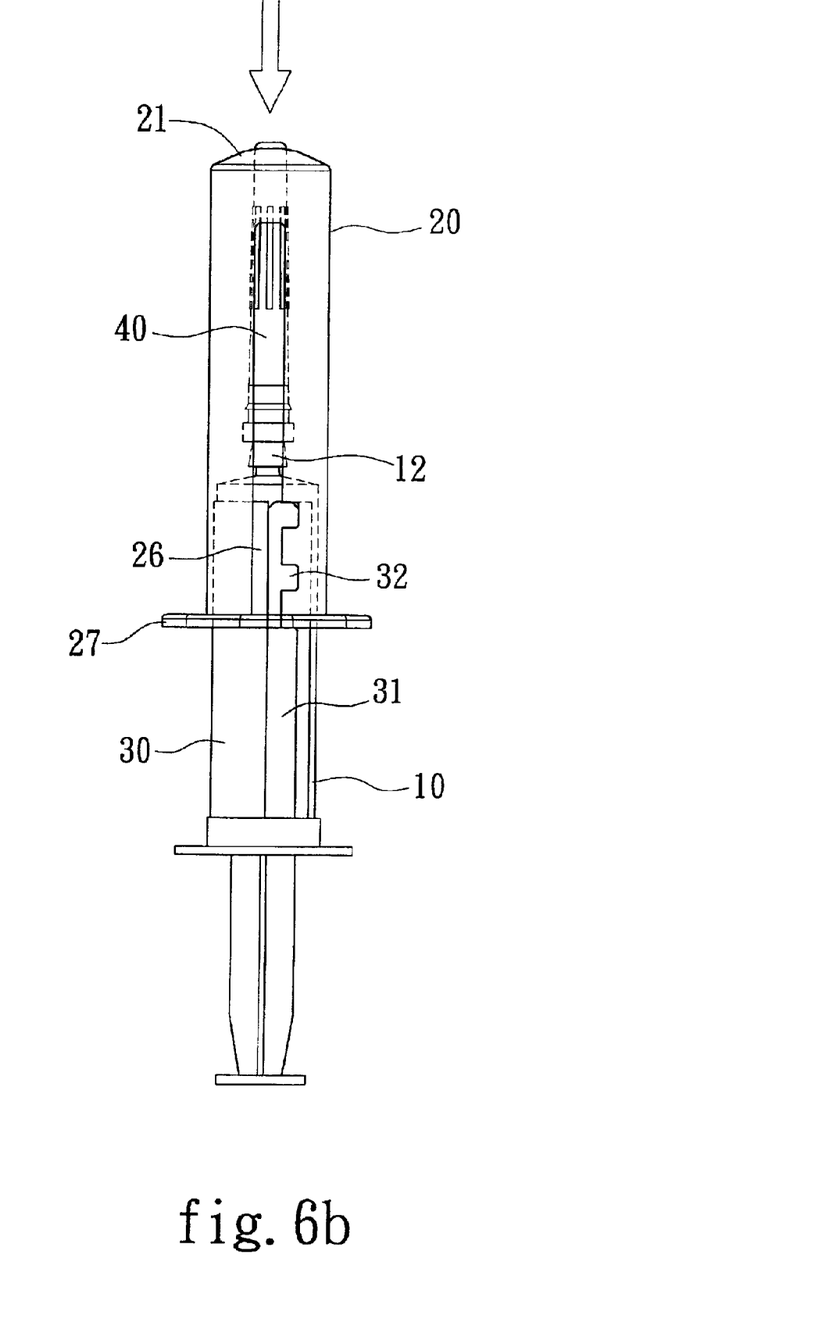
FIG. 6b is a schematic view showing pressing down of the needle cap of the embodiment of the present invention.

Referring to FIGS. 6a, 6b, when in taking out the syringe 10, the cut 23 on the conical surface 21 is pressed forcedly toward the center in the first place, the central hole 22 will be deformed to spread by providing of the cut 23 on the conical surface 21, thereby, the annular collar 50 can be removed from the external sleeve 20; now, the needle cap 40 is pressed down to render the annular collar 50 to be engaged with the needle 12 again. Then the syringe 10 is rotated to force the bendable positioning piece 26 to be raised to allow drawing out of the syringe 10.

Figure 7A:
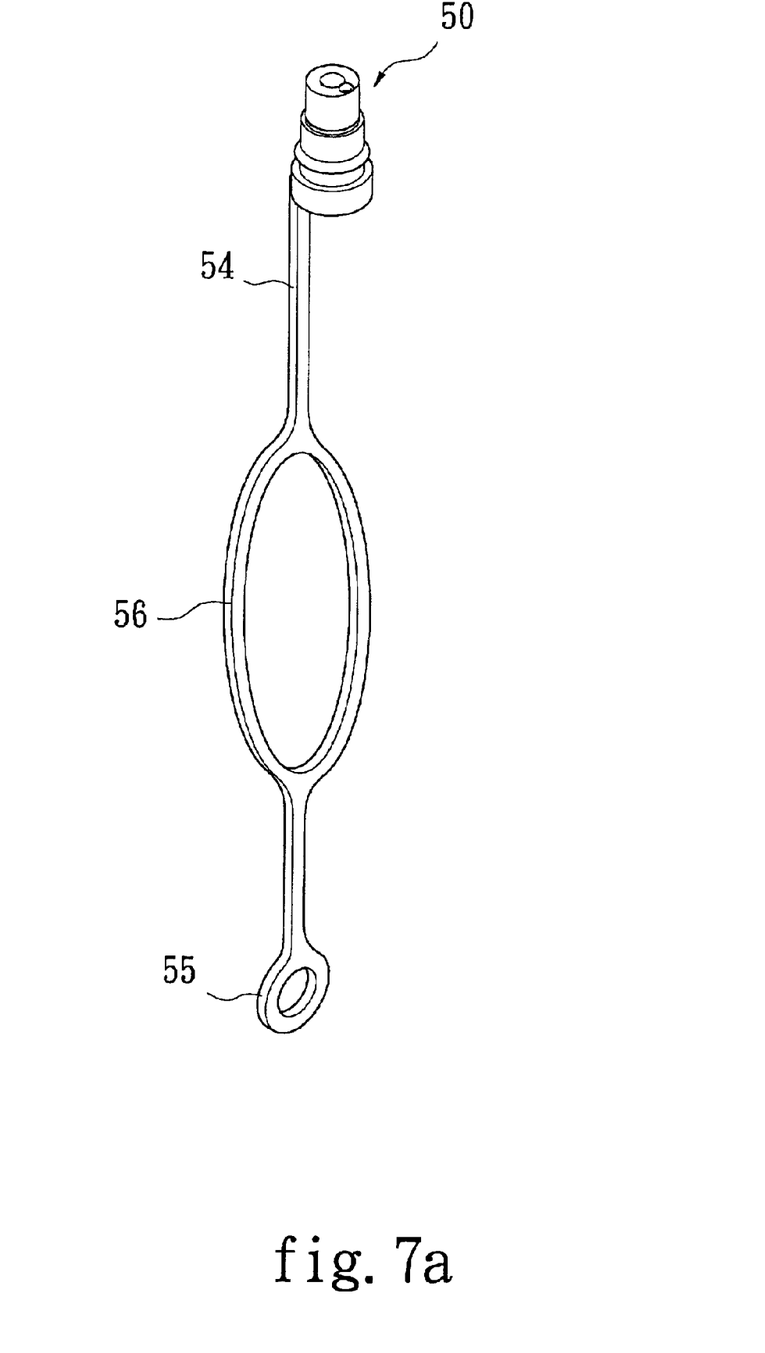
FIG. 7a is a perspective view of a second embodiment for the annular collar of the present invention.
Figure 8A:
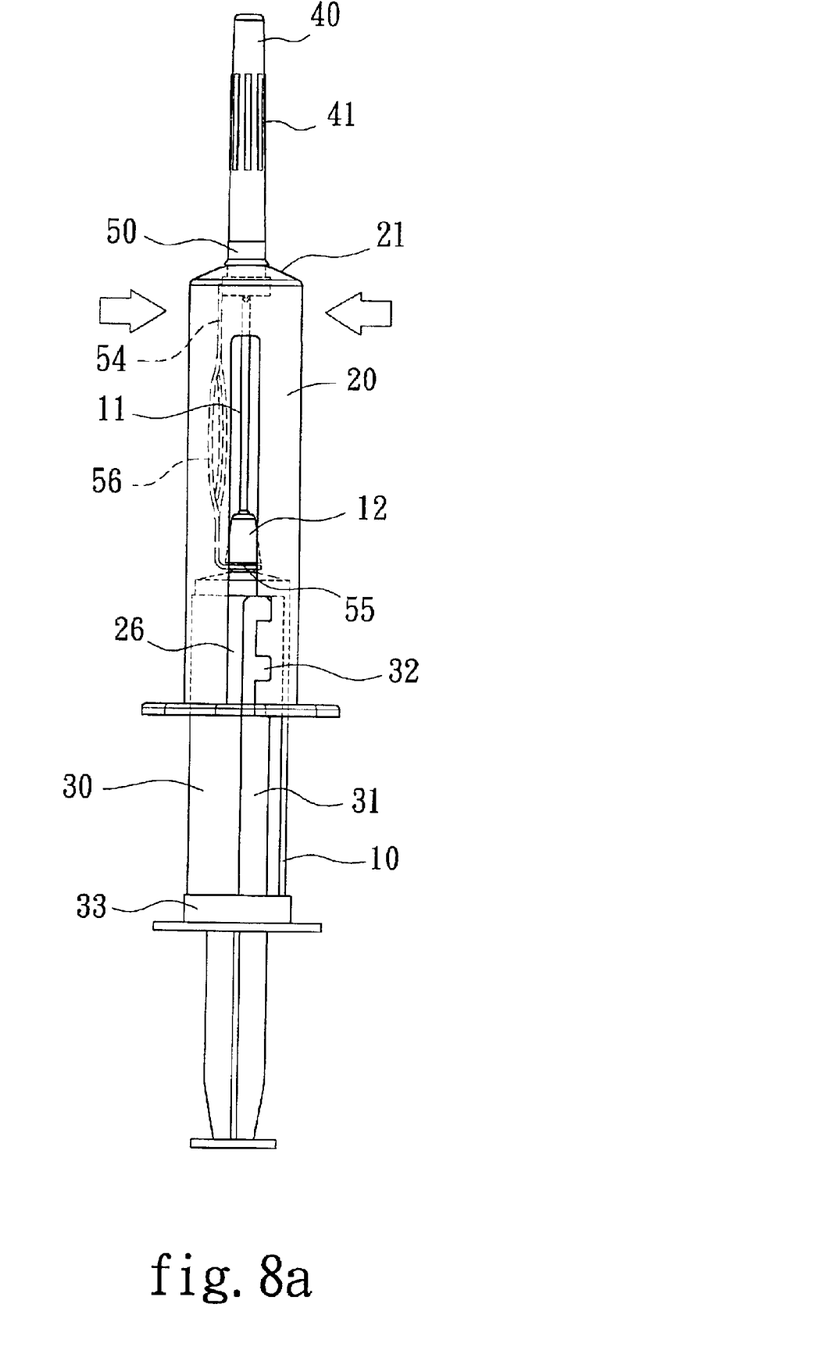
FIG. 8a is a schematic view showing use of the second embodiment of the present invention.
Figure 8B:
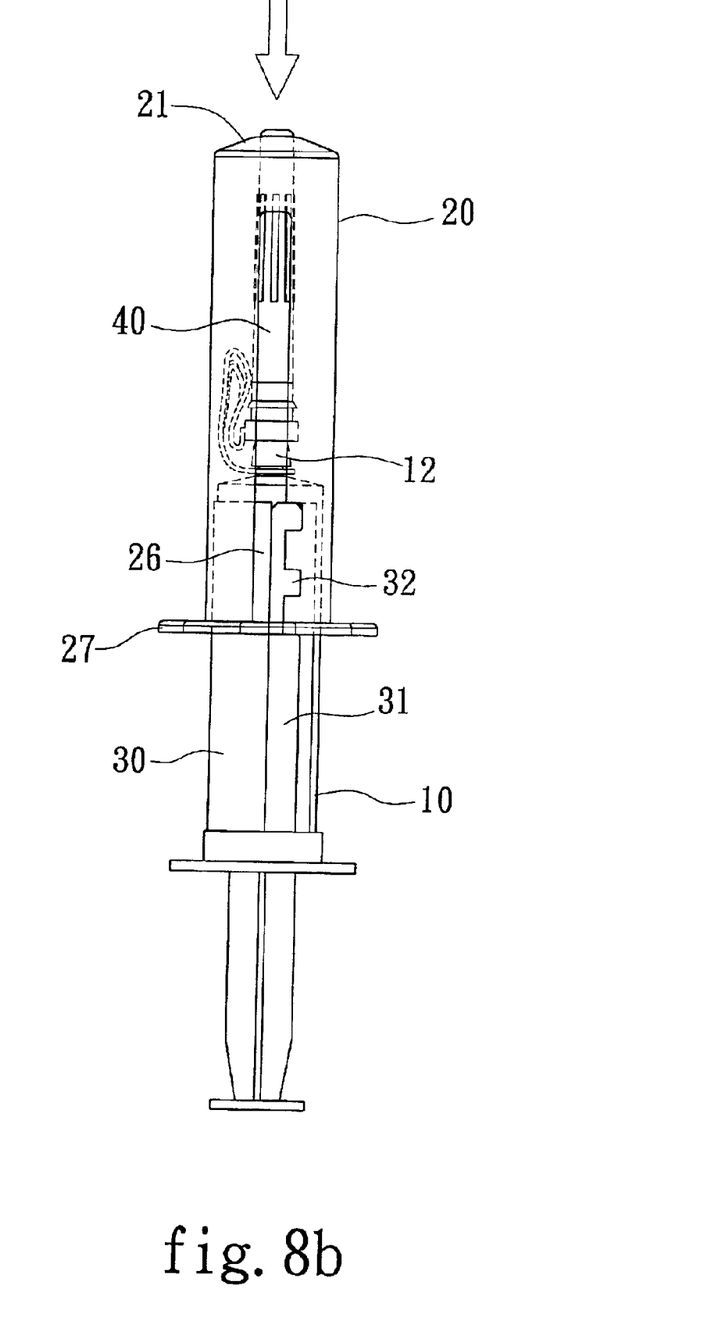
FIG. 8b is a schematic view showing completing of covering of the needle cap of the second embodiment of the present invention.

Referring to FIGS. 7a, 8a and 8b which show the second embodiment of the present invention, the second embodiment is mostly identical structurally to the above stated embodiment, except that the annular collar 50 is provided on the lower end thereof with a connecting member 54 which is an elongate strip with an engaging ring 55 on the tailing end thereof for engaging in a recess formed between the needle 12 and the syringe 10. The connecting member 54 is provided in the middle thereof with an elastic ring 56 of a suitable size, in order that when the connecting member 54 is pulled to stretch, appropriate elasticity thereof can be kept; in this way, after using the syringe 10, and when the needle cap 40 is put on to pull the syringe 10 outwardly, the elastic ring 56 provided on the annular collar 50 will be deformed by the pulling force, and thereby, certain elasticity exists between the needle 12 and the annular collar 50. In this case, when the annular collar 50 is to be connected with the needle 12 once more, it needs only to press the cut 23 forcedly toward the center to stretch out the conical surface 21, thereby, the annular collar 50 can be elastically and automatically contracted into the external sleeve 20; now, the needle cap 40 can be pressed down to render the annular collar 50 to be engaged with the needle 12 again, and the needle cap 40 can be safely put on the needle 12.

Figure 7B:
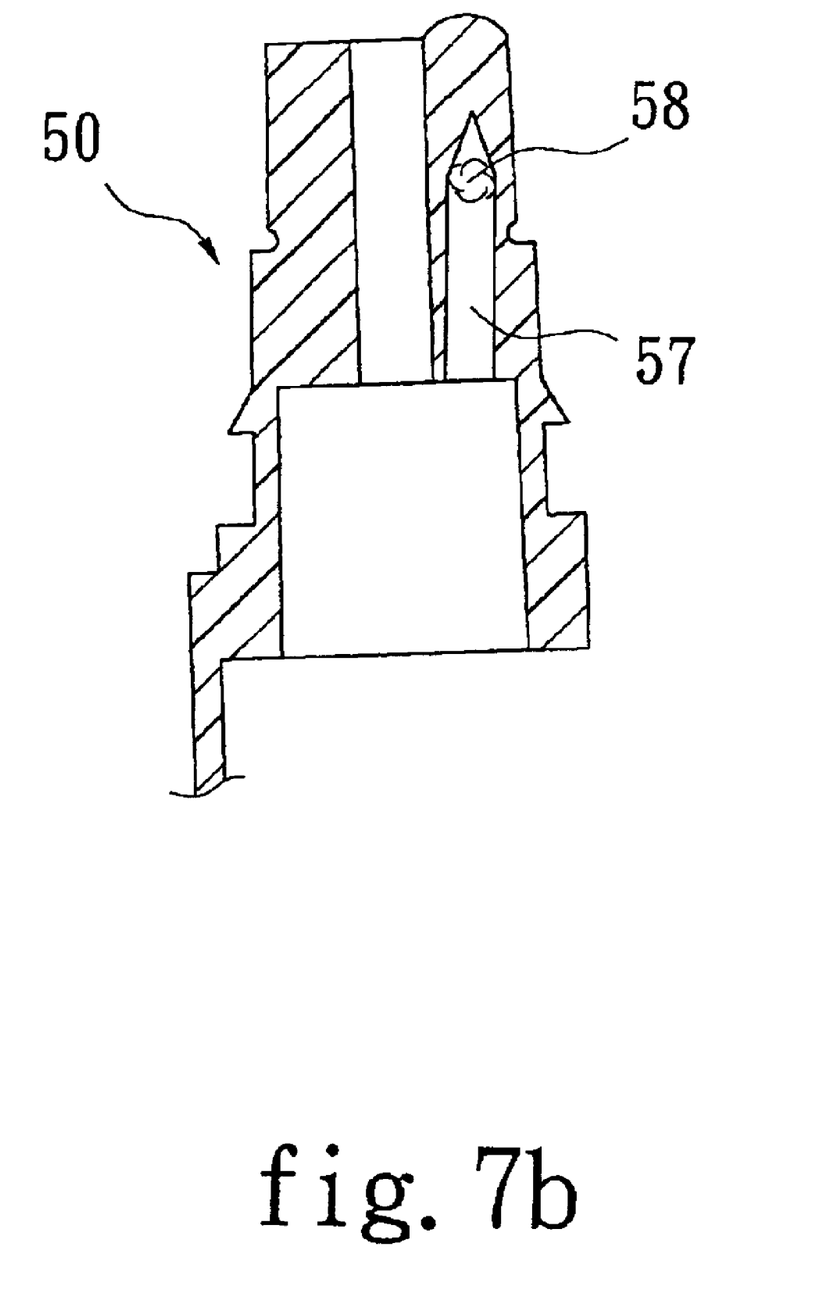
FIG. 7b is a sectional view of the second embodiment for the annular collar of the present invention.
Figure 9:
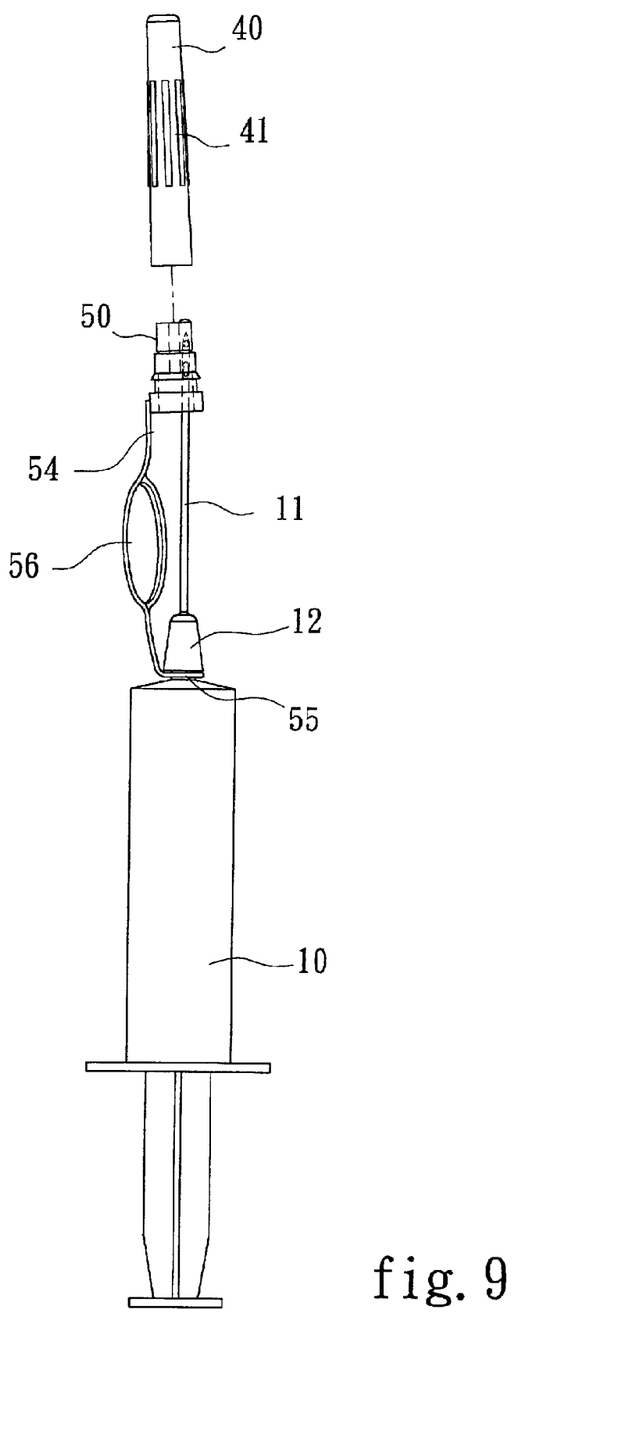
FIG. 9 is a schematic view showing use of the third embodiment of the present invention.

Referring to FIGS. 7b, 9, the second embodiment of the present invention can also be simplified to only use the annular collar 50 and the needle cap 40, wherein, the annular collar 50 is provided therein with a recess 57 as a receiving space for the point 11, the recess 57 is preferably provided at the position in opposition to that of the connecting member 54, and a sponge 58 with strong water absorbing ability can be provided in the receiving space. So that after injection of the syringe 10, it needs only to pull up the annular collar 50 with a hand for putting the point 11 in the recess 57, by certain degree of elasticity provided by the connecting member 54 connecting the annular collar 50 and the needle 12, the inner wall of the recess 57 of the annular collar 50 can tightly abut against the point 11 to prevent it from exposing. At this time, the needle cap 40 can be put back on the annular collar 50 without stabbing the finger of a user. Then the annular collar 50 and the needle cap 40 are slightly pushed forwardly to their correct positions, they can envelop the point 11 under the elastic force of the connecting member 54, and safe covering of the needle 12 can thus be effected. And by the fact that the recess 57 has therein the sponge 58 with strong water absorbing ability, remaining medicine or residual blood on the needlepoint 11 can be absorbed after injection to avoid environmental contamination and contagion of germs.

The present invention has the needle cap 40, the annular collar 50, the syringe clamp 30 and the external sleeve 20 combined without changing the original structure of the syringe 10, thereby the needle 12 is not exposed after using the syringe 10 or after being contaminated by germs, and thereby the medical staffs can be prevented from stabbing by the contaminated needle 12, an effect of protecting safety of the medical staffs can be obtained; and the external sleeve 20, the syringe clamp 30 and the fixing ring 33 can all be recovered for repeated using, thereby, cost of production can be reduced and an effect of environmental conservation can be obtained.

The present invention thereby has the following advantages:

1. The present invention is provided with an external sleeve to accommodate the dangerous needle point therein, this can effectively prevent the medical staff covering the needle cap from accident stabbing, and infection of germs to the medical staffs can be avoided, thereby, safety and practicality of use can be obtained.
2. The present invention suits needles of various lengths, by virtue that it is connected with a syringe by clamping, the needle cap can be put on the needle without a need of using a tool to change the original structure of the syringe. Thereby convenience of use can be obtained.
3. The external sleeve and the syringe clamp of the present invention can be easily mounted and dismantled as well as can be repeatedly used, thereby, the present invention has an economic as well as an environmental conservative effect, and practicality of use thereof can be obtained.

The present invention not only can get rid of the defects resided in the conventional syringes, but also can get the objects of accommodating the needle, safely coving the needle by providing the external sleeve and an annular collar. Therefore, practicality and convenience of the present invention are largely increased. The present invention can suit various kinds of syringes; thereby, the value of utility of the present invention can be assured.

The present invention has been described with a preferred embodiment thereof; however, the present invention is not limited to this. It will be apparent to those skilled in this art that various modifications or changes can be made to the elements of the present invention, and all such modifications and changes without departing from the spirit, scope and characteristic of this invention also fall within the scope of the appended claims and are intended to form part of this invention.

What is claimed is:

1. A safe cover device for a needle of a syringe comprising
  an external sleeve,
  a syringe clamp,
  a needle cap,
  and an annular collar mounted on a syringe,
  wherein said external sleeve is a cylinder having an internally receiving chamber in correspondence with a shape of said syringe, wherein said external sleeve comprises a conical surface on a distal end thereof having a central hole and an axial cut for allowing extension of said needle therein, said external sleeve having an elongated slide slot on a lateral side thereof;
  wherein said syringe clamp is a curved sheet with a curvature which is exactly for clamping said syringe, further said syringe having a protruding slide rail on the surface of said syringe clamp;
  wherein said needle cap is an elongate cylinder having a plurality of engaging nodes on an inner edge of a proximal opening thereof for making engagement of said needle cap with said annular collar;
  wherein said annular collar is a hollow cylinder with a central bore adapted for fitting exactly over said needle tightly, further said annular collar having an embedding groove and an engaging groove on an external surface thereof,
  wherein said embedding groove engages said needle cap with said annular collar and further said engaging groove is provided for engaging said conical surface of said external sleeve;
  wherein said syringe clamp clamping said syringe is adapted for sliding said external sleeve when said needle is completely retracted in said external sleeve, said needle cap is adapted for safely covering said needle to provide safety protection of a user.

2. The safe cover device as claimed in claim 1, wherein said external sleeve further comprises an elongate slide slot on which there are a plurality of engaging notches, wherein on an opposite side of the plurality of engaging notches of the slide slot comprises a bendable positioning piece, wherein on a bottom side of the slide slot comprises a plurality of flanges for holding in operation.

3. The safe cover device as claimed in claim 1, wherein said protruding slide rail of said syringe clamp further comprises a plurality of recessed portions to form a plurality of engaging blocks for engaging said slide slot of said external sleeve.

4. The safe cover device as claimed in claim 1, wherein said syringe clamp comprises a fixing ring on a tailing end of said syringe clamp for firmly clamping said syringe.

5. The safe cover device as claimed in claim 1, further comprising
  a connecting member having a proximal and distal end,
  said annular collar comprises a proximal and distal end,
  wherein the distal end of the connecting member is attached to the proximal end of the annular collar and an engaging ring is at the proximal end of the connecting member and said connecting member comprises an elastic ring in the middle of the connecting member.

6. The safe cover device as claimed in claim 1, wherein said annular collar comprises a recess therein for tightly abutting against the point of said needle.

7. The safe cover device as claimed in claim 6, wherein said recess comprises a sponge therein.

* * * * *